United States Patent
Schwartz et al.

(10) Patent No.: US 11,002,718 B2
(45) Date of Patent: May 11, 2021

(54) GAS SENSOR

(71) Applicant: Palo Alto Research Center Incorporated, Palo Alto, CA (US)

(72) Inventors: David Eric Schwartz, Concord, MA (US); Jianer Bao, Sunnyvale, CA (US)

(73) Assignee: PALO ALTO RESEARCH CENTER INCORPORATED, Palo Alto, CA (US)

( * ) Notice: Subject to any disclaimer, the term of this patent is extended or adjusted under 35 U.S.C. 154(b) by 117 days.

(21) Appl. No.: 15/991,371

(22) Filed: May 29, 2018

(65) Prior Publication Data
US 2019/0369075 A1 Dec. 5, 2019

(51) Int. Cl.
G01N 33/00 (2006.01)
G01N 30/64 (2006.01)
G01N 31/22 (2006.01)
G01N 27/12 (2006.01)

(52) U.S. Cl.
CPC ....... G01N 33/0009 (2013.01); G01N 27/127 (2013.01); G01N 30/64 (2013.01); G01N 31/22 (2013.01); G01N 33/0006 (2013.01); G01N 2033/0072 (2013.01)

(58) Field of Classification Search
CPC .......... G01N 33/0009; G01N 33/0006; G01N 27/127; G01N 30/64; G01N 31/22
USPC ........................................................ 73/23.2
See application file for complete search history.

(56) References Cited

U.S. PATENT DOCUMENTS

| | | | |
|---|---|---|---|
| 6,844,742 B2 * | 1/2005 | Centanni | G01N 27/221 204/403.01 |
| 6,933,733 B2 * | 8/2005 | Korenev | G01N 27/06 324/663 |
| 7,785,894 B2 * | 8/2010 | Smolander | G01N 31/223 436/166 |
| 9,049,663 B2 * | 6/2015 | Rabii | H04W 52/0254 |
| 2002/0017126 A1 * | 2/2002 | DiMeo, Jr. | G01N 21/59 73/31.05 |
| 2007/0235773 A1 * | 10/2007 | Eisele | G01N 27/4143 257/253 |

(Continued)

OTHER PUBLICATIONS

New Jersey Department of Health and Senior Services, "Hazardous Substance Fact Sheet," Mustard Gas, 6 pages, http://nj.gov/health/eoh/rtkweb/documents/fs/1319.pdf.

(Continued)

Primary Examiner — Nimeshkumar D Patel
Assistant Examiner — Jean F Morello
(74) Attorney, Agent, or Firm — Fay Sharpe LLP

(57) ABSTRACT

Gas sensors for the detection of rare events consume very little or no power. The sensors include materials that interact with a target gas. Accumulation of the target gas on the sensor materials leads to a change in electrical properties of the sensor. The sensors may have high gain, meaning that a large electrical change is induced upon gas accumulation. The sensor might change from an extremely high resistance (open circuit) to a measurably low resistance, or it might change from a relatively low capacitance to a high capacitance. The gas sensors are connected to electronics that can transmit an alarm signal after gas has been detected. The electronics may be in a low power sleep mode until awakened by a signal from the sensor.

20 Claims, 6 Drawing Sheets

(56) References Cited

U.S. PATENT DOCUMENTS

| | | | |
|---|---|---|---|
| 2009/0261987 A1* | 10/2009 | Sun | G01N 35/00732 340/870.07 |
| 2010/0007890 A1* | 1/2010 | Graf | G01N 21/3504 356/437 |
| 2010/0170325 A1* | 7/2010 | Ren | G01N 27/127 73/31.05 |
| 2014/0326615 A1* | 11/2014 | Kocanda | G01N 27/02 205/775 |
| 2016/0018321 A1* | 1/2016 | Moenkemoeller | G01N 21/3504 250/341.1 |
| 2016/0091445 A1* | 3/2016 | Ayesh | G01N 27/127 324/693 |
| 2016/0238578 A1* | 8/2016 | Lakhotia | G01N 33/005 |
| 2017/0026722 A1* | 1/2017 | Schwartz | H04W 4/70 |
| 2017/0285211 A1* | 10/2017 | Monteiro | G01V 3/24 |
| 2019/0011412 A1* | 1/2019 | Jung | H01L 21/28 |
| 2019/0035253 A1* | 1/2019 | Jones, II | H04Q 9/00 |

OTHER PUBLICATIONS

M.V. Buskirk, "Conductive Bridging RAM(CBRAM™): A Scalable, Low Power and High Performance Resistive Memory Technology Platform," Interconnect Technology Conference, 2012 IEEE International, DOI: 10.1109/IITC.2012.6251588, 3 pages.

M. Tabib-Azar, "CuS and AgS Solid-Electrochemical Cells as Non-Volatile Memory Devices," 7th Microfabricated Systems and MEMS Proceedings, Pennington, NJ, 2004, 1 page.

T. Xu et al., "Self-Assembled Monolayer-Enhanced Hydrogen Sensing with Ultrathin Palladium Films," Applied Physics Letters 86, 203104, 2005, 3 pages.

F. Favier et al. "Hydrogen Sensors and Switches from Electrodeposited Palladium Mesowire Arrays," Science, vol. 293, 2001, pp. 2227-2231.

NASA Earth Observatory, "Global Fire Monitoring, Trace Gas Emissions," Oct. 22, 1999, 3 pages, https://earthobservatory.nasa.gov/Features/GlobalFire/fire_3.php.

NASA Earth Observatory, Global Fire Monitoring, NASA and NOAA Missions for Monitoring Global Fires, Oct. 22, 1999, 6 pages, https://earthobservatory.nasa.gov/Features/GlobalFire/fire_5.php.

F.A. Lewis, "The Hydrides of Palladium and Palladium Alloys," Platinum Metals Rev., 1960, 5 pages.

Musings on Iraq, "A History of Oil Smuggling in Iraq," Aug. 17, 2010, 17 pages, http://musingsoniraq.blogspot.com/2010/08/history-of-oil-smuggling-in-iraq.html.

M. Myers, "The Performance Implications of Silver as a Contact Finish in Traditionally Gold Finished Contact Applications," Proceedings of the 55th IEEE HOLM 2009, Conference on Electrical Contacts, Sep. 2009, 9 pages.

S. P. Urbanski et al., "Chemical Composition of Wildland Fire Emissions," Chapter 4, Developments in Environmental Science, vol. 8, 2009, 29 pages.

Bureau of Transportation Statistics, "Table 1-10: U.S. Oil and Gas Pipeline Mileage," https://www.rita.dot.gov/bts/sites/rita.dot.gov.bts/files/publications/national_transportation_statistics/html/table_01_10.html, May 21, 2017, 3 pages.

Chris Dalby, "These Are the 5 Countries Most Plagued by Oil Theft," http://oilprice.com/Energy/Energy-General/These-Are-The-5-Countries-Most-Plagued-by-Oil-Theft.html, Jul. 3, 2014, 5 pages.

Bill Hoagland, "Hydrogen leak detection—low cost distributed gas sensors," 56 pages.

X.Q. Zeng et al., "Hydrogen Gas Sensing with Networks of Ultrasmall Palladium Nanowires Formed on Filtration Membranes," Nano Letters, 11, 2011, pp. 262-268.

* cited by examiner

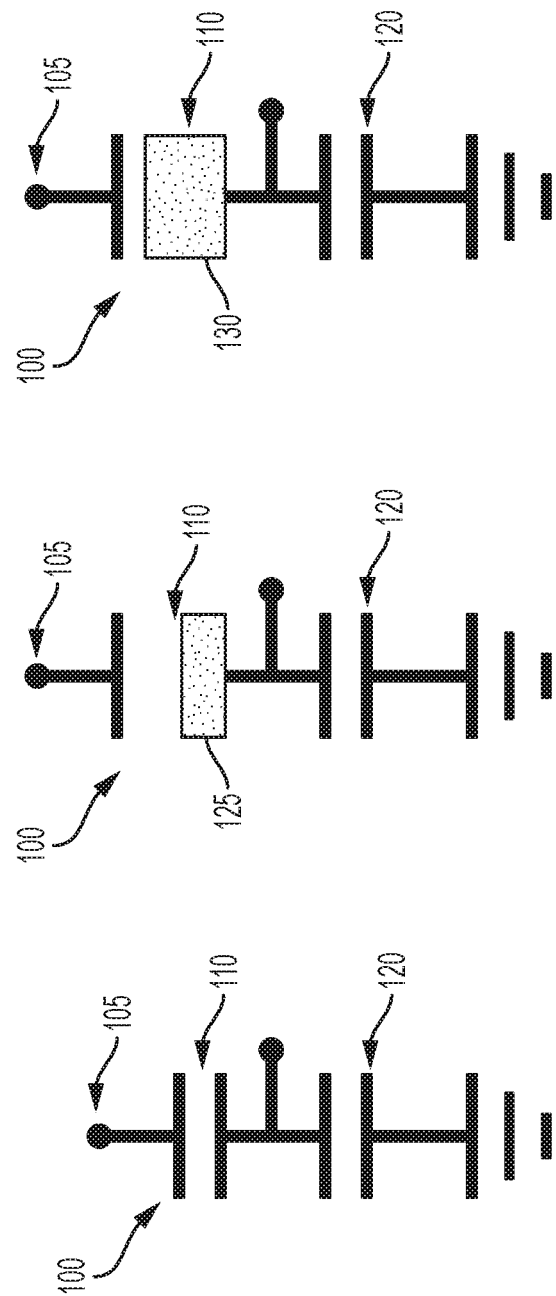

GAS SENSOR

BACKGROUND

The present disclosure relates to gas sensors that consume very little or no power. The gas sensors are useful for detecting rare events.

There are a number of key defense, civilian, and environmental applications for gas sensors capable of detecting gases indicative of rare events. These include early detection of chemical warfare agents, industrial safety monitoring, detecting leaks from natural gas or petroleum pipelines, detection of oil or gas theft from pipelines or other infrastructure, detecting hydrogen leaks from hydrogen fueling stations and infrastructure, early forest fire warnings, detection of electrolytic hydrogen generation (in submarines, for example), and hazardous gas detection including accidental and deliberate dispersal of chemical warfare agents and Toxic Industrial Chemicals (TICs). Another use is the detection of the presence of vehicles by means of their exhaust gas. For these uses, sensors must be deployed over very large and sometimes diverse areas, often with limited power availability. Hazardous events are extremely rare, and continuous monitoring with conventional techniques is battery-lifetime limited.

It would be desirable to develop new systems and methods for detecting gases, particularly for detecting gases indicative of the occurrence of rare events.

BRIEF DESCRIPTION

The present disclosure relates to a gas sensor.

Disclosed, in some embodiments, is a system for detecting a target gas. The system includes a sensor which exhibits an electrical property, wherein the electrical property changes in the presence of the target gas; and a signal generator that generates a signal when a change in the electrical property passes a predetermined threshold value.

In some embodiments, the sensor has a very low power consumption.

The sensor may include a sensor material which chemically reacts with or expands in the presence of the target gas.

In some embodiments, the signal is a wireless signal, a wired signal, an audio signal, or a visual signal.

Optionally, the system further includes a second sensor for verifying the presence of the target gas, wherein the signal is configured to activate the second sensor; and an alarm generator for generating an alarm if the second sensor verifies the presence of the target gas.

The system may further include a wearable substrate, wherein the sensor is secured to the wearable substrate.

In some embodiments, the sensor includes a fixed capacitor and a variable capacitor, wherein a capacitance of the variable capacitor increases with increasing exposure to the target gas.

Optionally, the variable capacitor comprises palladium and wherein the target gas is hydrogen or methane.

The sensor may include nanoparticles. In some embodiments, the nanoparticles are silver nanoparticles and wherein the target gas is a sulfide gas.

Optionally, the sensor includes a first wire section and a second wire section. A nanoscale gap exists between the first wire section and the second wire section and the sensor is configured such that accumulated exposure to the target gas causes the nanoscale gap to be bridged.

The first wire section and the second wire section may contain palladium and the target gas may be hydrogen or methane.

In some embodiments, the sensor includes a first plate, a second plate, and a dendrite having a length and extending from one of the first plate and the second plate. A gap having a distance exists between the first plate and the second plate and the length is less than the distance unless an accumulated exposure to the target gas exceeds a threshold value.

Optionally, the first plate contains gold, the second plate contains silver or gold; the dendrite contains silver; and the target gas is a sulfide gas.

Disclosed in other embodiments is a system for detecting a target gas including: a low power sensor which exhibits an electrical property, wherein the electrical property changes in the presence of the target gas, wherein the low power sensor is configured to generate a wake-up signal when the electrical property passes a predetermined threshold value; and an electronic component in communication with the low power sensor and configured to operate in a sleep mode until the wake-up signal is received.

The electronic component may include an alarm.

In some embodiments, the electronic component include a higher power sensor.

Optionally, the higher power sensor measures the presence and/or concentration of the target gas.

The higher power sensor may be configured to generate an alarm signal upon verification of the presence of the target gas.

Disclosed in further embodiments is a method for detecting a target gas. The method includes providing a system for detecting the target gas. The system includes a lower power sensor which exhibits an electrical property, wherein the electrical property changes in the presence of the target gas, wherein the lower power sensor is configured to generate a wake-up signal when the electrical property passes a predetermined threshold value; and an electronic component in communication with the low power sensor and configured to operate in a sleep mode until the wake-up signal is received. The electronic component includes at least one of the following: an alarm generator for generating an alarm system; and a higher power sensor configured to continuously measure the presence of the target gas and communicate measurements off-site.

These and other non-limiting characteristics are more particularly described below.

BRIEF DESCRIPTION OF THE DRAWINGS

The following is a brief description of the drawings, which are presented for the purposes of illustrating the exemplary embodiments disclosed herein and not for the purposes of limiting the same.

FIGS. 1-3 are schematic illustrations of a zero-power capacitive sensor in accordance with some embodiments of the present disclosure.

DETAILED DESCRIPTION

Figure 5:
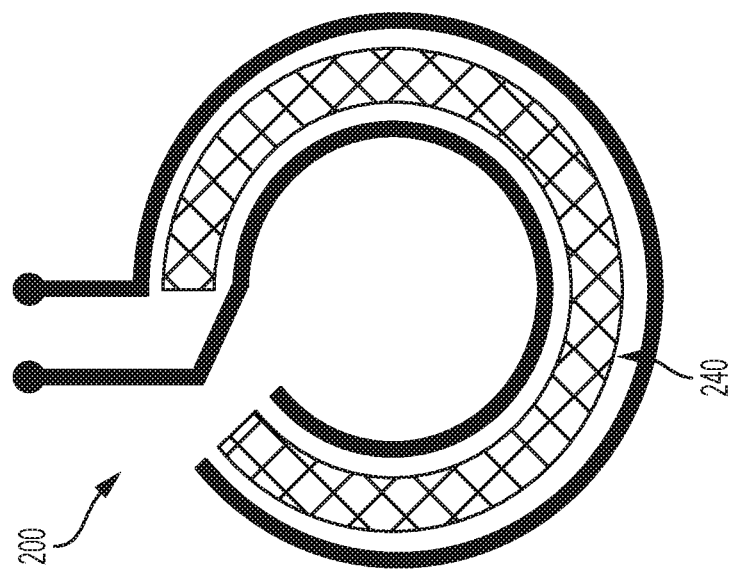
FIGS. 4 and 5 schematically illustrate a capacitance-based sensor which functions through dielectric constant change in accordance with some embodiments of the present disclosure.

A more complete understanding of the systems and methods disclosed herein can be obtained by reference to the accompanying drawings. These figures are merely schematic representations based on convenience and the ease of demonstrating the existing art and/or the present development, and are, therefore, not intended to indicate relative size and dimensions of the assemblies or components thereof.

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent can be used in practice or testing of the present disclosure. The materials, methods, and articles disclosed herein are illustrative only and not intended to be limiting.

The singular forms "a," "an," and "the" include plural referents unless the context clearly dictates otherwise.

As used in the specification and in the claims, the term "comprising" may include the embodiments "consisting of" and "consisting essentially of." The terms "comprise(s)," "include(s)," "having," "has," "can," "contain(s)," and variants thereof, as used herein, are intended to be open-ended transitional phrases that require the presence of the named ingredients/steps and permit the presence of other ingredients/steps. However, such description should be construed as also describing compositions, mixtures, or processes as "consisting of" and "consisting essentially of" the enumerated ingredients/steps, which allows the presence of only the named ingredients/steps, along with any impurities that might result therefrom, and excludes other ingredients/steps.

Unless indicated to the contrary, the numerical values in the specification should be understood to include numerical values which are the same when reduced to the same number of significant figures and numerical values which differ from the stated value by less than the experimental error of the conventional measurement technique of the type used to determine the particular value.

All ranges disclosed herein are inclusive of the recited endpoint and independently combinable (for example, the range of "from 2 to 10" is inclusive of the endpoints, 2 and 10, and all the intermediate values). The endpoints of the ranges and any values disclosed herein are not limited to the precise range or value; they are sufficiently imprecise to include values approximating these ranges and/or values.

As used herein, approximating language may be applied to modify any quantitative representation that may vary without resulting in a change in the basic function to which it is related. Accordingly, a value modified by a term or terms, such as "about" and "substantially," may not be limited to the precise value specified, in some cases. The modifier "about" should also be considered as disclosing the range defined by the absolute values of the two endpoints. For example, the expression "from about 2 to about 4" also discloses the range "from 2 to 4." The term "about" may refer to plus or minus 10% of the indicated number. For example, "about 10%" may indicate a range of 9% to 11%, and "about 1" may mean from 0.9-1.1.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

The present disclosure relates to gas sensors. Generally, the sensors comprise materials that interact with a target gas. Accumulation of target gas on the sensor materials leads to a change in electrical properties of the sensor. Since the sensors measure the accumulation of gases, they may be triggered by exposure to very low concentrations. Generally, the sensors have high gain, meaning that a large electrical change is induced upon accumulated gas exposure. For example, the sensor might change from an extremely high resistance (open circuit) to a measurably low resistance, or it might change from a relatively low capacitance to a high capacitance. The gas sensors are connected to electronics that can transmit an alarm signal after gas has been detected. The electronics may be in a low power state (e.g., stand-by mode) until receiving a wake-up signal from the sensor.

The gas sensors can additionally be used for wearable applications. Fabricating sensors on flexible substrates enables lightweight, comfortable wearable devices that can warn the wearer of potential exposure to a dangerous or toxic gas.

Early, broad-area, easily deployable detection of toxic gases and chemical warfare agents is critical to civilian and warfighter safety. One class of gases for which chemical detection is well suited is sulfur-based toxins, including mustard gas (sulfur mustard) and hydrogen sulfide ($H_2S$), which have been used as chemical weapons and have human exposure limits of 60 ppb over ten minutes, and 5 ppm over 15 minutes, respectively. $H_2S$ is also a byproduct of natural gas production and is present in raw natural gas at variable and unpredictable concentrations. Sulfides and other Toxic Industrial Chemicals (TICs) pose hazards from accidents and as weapons of opportunity, in which processing, storage and transportation of these elements can multiply the impact of terrorist attacks, just as the Sep. 11, 2001 terrorist attackers used full tanks of jet fuel to make missiles out of civilian aircraft. Many TICs are sulfur-based (e.g., carbon disulfide, sulfur dioxide ($SO_2$), sulfur trioxide ($SO_3$), sulfuryl chloride, methyl mercaptan, n-octyl mercaptan, perchloromethyl mercaptan, ethyl chlorothioformate, sulfuryl fluoride, sulfuric acid, carbonyl sulfide, chlorosulfonic acid, methanesulfonyl chloride, parathion, and dimethyl sulfate). Many can be detected through reactive chemistry approaches.

A zero-power sensor network deployed to provide wide area, early warning of either accidental or deliberate dispersal of TICs and chemical weapons would be a valuable tool in the defense and homeland security kit. Such a system would allow dispersed, wide area, persistent sensing around vulnerable and critical locations (e.g. military barracks and headquarters, civilian critical infrastructure and densely populated areas, natural gas wells, pipelines, and facilities, especially where they are near other vulnerable areas). Concepts of operations for deployment include disperse-and-forget, vehicle-mounted and wearable options. For disperse-and-forget, networks of sensors can be deployed at critical/vulnerable sites to provide early warning of weapons and TICs escaping an area they are supposed to be in or entering an area they are not. Some viable use-cases include perimeters of chemical plants (to detect exit), perimeters of forward operating bases (to detect attacks), interiors of public transit, and in buildings, including in living and working spaces and as an active component of air handling systems. Vehicle and transportation system uses include the exterior of tankers and shipping containers as well as Department of Defense (DoD) and first responder vehicles. While on-vehicle use cases can use powered sensors, having a sensor that operates in motor pools without draining vehicle batteries could provide additional security. Similarly for wearable sensors, battery-powered versions may be available but add to the logistics burden of the dismounted soldier and the first responder. An ad hoc mesh network of wearable sensors that does not add to the size, weight and power (SWaP) of the kit for the soldier/first responder is desirable.

The integrity of the greater than 1.6 million miles of natural gas pipeline and greater than 160 thousand miles of petroleum pipeline in the United States is essential to national security. Oil theft is also a significant global concern including in key areas of U.S. interest, such as Iraq. Current technologies are insufficient for monitoring vast pipeline networks in a cost effective way. A zero-power hydrocarbon sensor combined with wake-up electronics could remain dormant until a gas leak was detected, at which time a communication would be sent to an operations center, which could respond appropriately either with further investigation or through deployment of a maintenance team, as the situation requires. Concepts of operations for deployment are similar as discussed above: disperse-and-forget (integrated with pipeline infrastructure), vehicle-mounted (on systems that operate near the pipelines) and wearable options (for maintainers both as early warning and as dosimeters for crews sent out after dispersed sensors indicate a problem).

Hydrogen is the primary feedstock for ammonia production and is becoming an increasingly important fuel source. It is colorless and odorless and difficult to contain, yet extremely flammable with a low ignition energy. Hydrogen sensor networks deployed around hydrogen fueling stations, and other infrastructure, can prevent catastrophic explosions. Concepts of operations for deployment again include disperse-and-forget (integrated with pipeline, storage and fueling infrastructure), vehicle-mounted (on bulk transportation systems and on hydrogen fueled vehicles) and wearable options (for fuel station operators and maintenance crews).

The wide variety of emissions from wildfires (greenhouse gases, photochemically reactive compounds, particulates, etc.) are believed to significantly influence the chemical composition of the air and the earth's climate system. These emissions contribute to air pollution and are detrimental to human health and ecosystems. Today, burning of tropical forest contributes to about 30% of total emissions.

Wild fires can also cause home and life losses for many who live nearby. Current approaches for wildfire monitoring primarily use satellites. One of NASA and NOAA's missions is to monitor global fires. However, no one system is optimal for fire monitoring, and sensor fusion is needed to enhance current systems. Incomplete combustion leads to the emission of methane ($CH_4$). Early detection of wildfires through detection of $CH_4$ through disperse-and-forget sensing could be very beneficial and prevent huge economic losses.

Some embodiments for achieving zero-power sensing include a capacitive voltage divider in which the capacitance of one capacitor is a function of gas accumulation. This can be a physical change, such as the expansion of the dielectric or conductor as gas is absorbed, or a chemical change, either spontaneous or through a redox or other chemical reaction. For example, in non-limiting embodiments, palladium (Pd) metal expands in the presence of hydrogen ($H_2$). $H_2$ dissociates into H atoms at the Pd surface which diffuse into Pd to form two solid phases, leading to volume expansion. At an H/Pd atomic ratio of 0.03, a volume expansion of 0.8% has been observed. The corresponding $H_2$ equilibrium pressure/concentration at that ratio is well below 0.1%. In the detection range that is needed for safety, up to 10% volume expansion is possible.

An example of a zero-power sensor 100 is shown in FIGS. 1-3. A voltage divider comprising a sensing capacitor 110 (having capacitance $C_1$) and a fixed capacitor 120 (having capacitance $C_2$) is connected to a battery voltage source 105 (having voltage $V^+$). Sensor power consumption is limited to current leakage through the fixed capacitor. In some embodiments, the sensor power consumption is extremely low (e.g., as low as about 1 µW or less). One plate 125 of the sensor capacitor is composed of a material which expands in the presence of the target gas. As the material absorbs the target gas, it expands, reducing the gap, increasing the capacitance and the output voltage $V_T$. When $V_T$ passes the trigger threshold in the expanded state of the plate 130, the sensor network is awakened to communicate an alarm, optionally after verifying the gas presence with a higher-power conventional detector. FIG. 2 illustrates the sensor in a first state wherein $C_1$ is low and $V_T$ is below the trigger threshold. FIG. 3 illustrates the sensor in a second state wherein $C_1$ is high and $V_T$ is above the trigger threshold. In some embodiments, the sensor capacitor contains Pd or a Pd-containing alloy. The target gas may be $H_2$.

Figure 4:
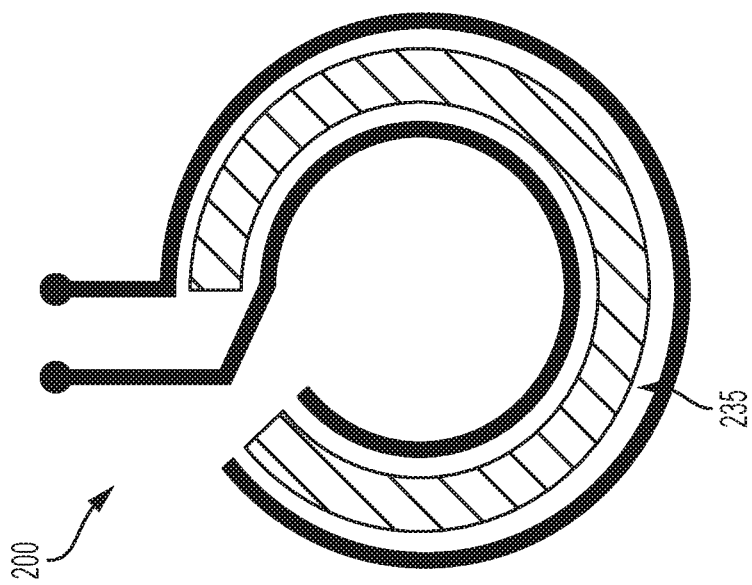

FIGS. 4-5 show a diagram of a capacitance-based sensor 200, capable of detecting a target gas. Here, a reactive dielectric material (e.g., a paste) 235 is deposited between the capacitor electrodes. As the reactive dielectric material reacts with the target gas, a product having a different dielectric constant is formed 240. The associated change in capacitance can be converted to a voltage change to trigger the detector. In some embodiments, the reactive dielectric material contains silver (Ag). The target gas may contain $H_2S$, sulfur mustard, and/or other sulfur compounds known to tarnish the paste material. The reactive dielectric material may contain nanoparticles. In some embodiments, the dielectric constant is changed by an order of magnitude or more (e.g., from about 0.4 to about 6). The reaction product may be silver sulfide ($Ag_2S$).

There is also a significant volume expansion (~166.6%) associated with the conversion from Ag (density 10.49 g/cc) to $Ag_2S$ (7.23 g/cc), which can connect the dispersed Ag nanoparticles to further enhance the dielectric change (from an Ag-air composite to $Ag_2S$). Both the capacitive coil and the silver paste can be printed on a flexible substrate, enabling lightweight, comfortable wearable sensor implementations.

Figure 6:
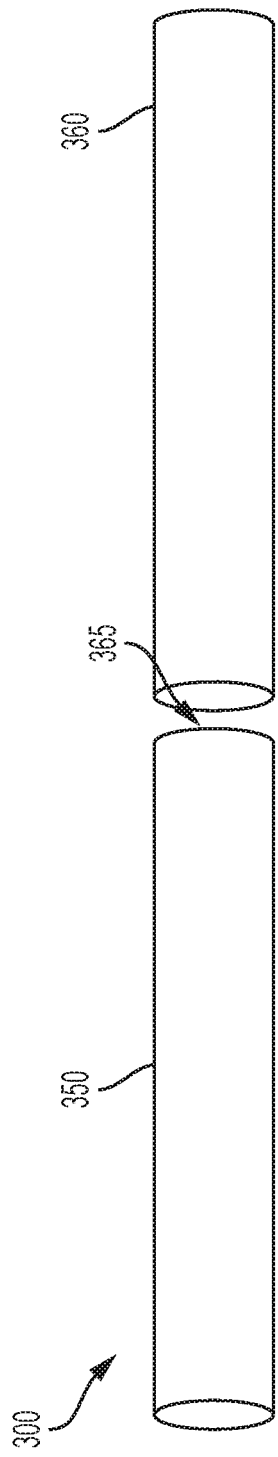
FIGS. 6 and 7 schematically illustrate a conductive bridge formed when nanostructures expand upon exposure to a target gas in accordance with some embodiments of the present disclosure.
Figure 7:
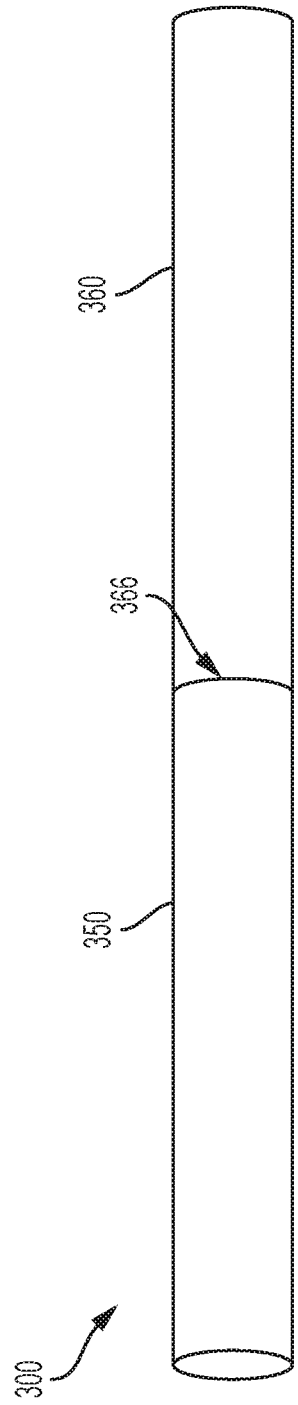

Other mechanisms are also possible. For example, the expansion of a sensor material under exposure to a target gas can fully bridge a nanometric gap 365 in a mesowire array or nanowire network 300 as shown in FIGS. 6-7. In these embodiments, the sensor may be referred to as a conductive bridge sensor.

FIG. 6 illustrates a network 300 including a first wire segment 350 and a second wire segment 360 prior to exposure to a target gas (e.g., $H_2$, $CH_4$, etc.). A nanometric gap 365 can be seen between segments 350, 360. The wire segments 350, 360 may contain Pd or a Pd-containing alloy in some embodiments.

FIG. 7 illustrates the network 300 after exposure to the target gas. As shown, the gap has been shorted 366.

It is possible to control the nano-gap distance 365 and tune the critical concentration level. For example, coating the substrate with a self-assembled monolayer (SAM) of siloxane before sputtering Pd can generate a consistent gap size. In some embodiments, a detection sensitivity of about 25-ppm $H_2$ can be achieved using this fabrication process. Many other fabrication approaches can also be considered. This mechanism can also be used for methane or natural gas detection as Pd acts as a catalyst for cracking the C—H bonds in $CH_4$, freeing hydrogen atoms which then expand the Pd. It may also be possible to engineer this to detect volatile organic compounds and other hydrocarbon gases.

Figure 8:
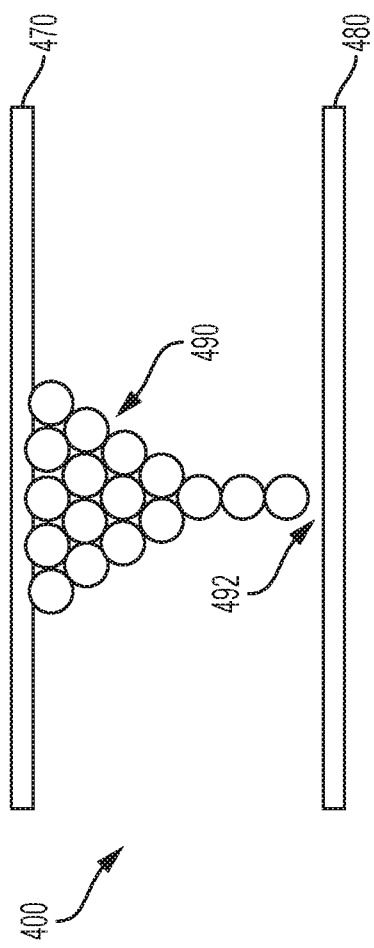
FIGS. 8 and 9 are schematic illustrations of a conductive nano-gap bridge gas sensor in a base state; and in an expanded state upon exposure to a target gas, respectively, in accordance with some embodiments of the present disclosure.
Figure 9:
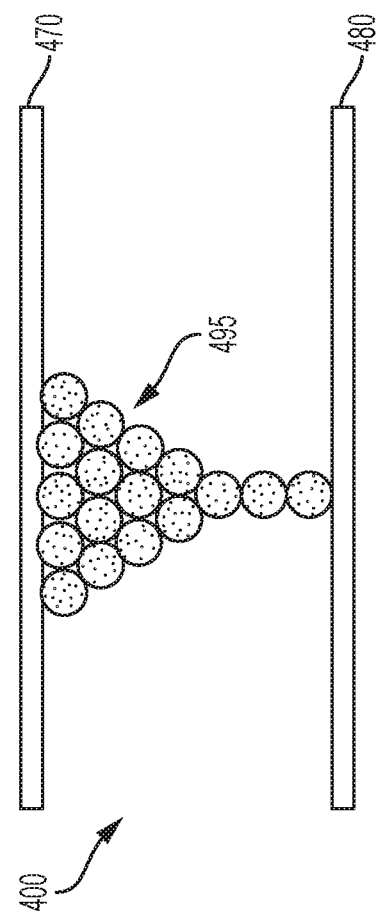

A conductive switch can also be formed based on a redox couple for target gas detection. In some embodiments, the redox couple is a silver/silver sulfide ($Ag/Ag_2S$) redox couple. The target gas may be a sulfide gas. FIGS. 8-9 show an illustration using conductive switch (e.g., a dendrite) 490. The depicted sensor 400 includes a first plate 470 (e.g., a gold plate) and a second plate 480 (e.g., a silver or gold plate). By electrochemically controlling the gap distance 492 of the conductive switch 490 tip and plate 480 during fabrication, an open circuit can be formed to serve as the dormant zero-power state (FIG. 8). When the switch (e.g., Ag switch) 490 is exposed to the target gas (e.g., sulfide gas), the chemical reaction will lead to the formation of the connected conductive switch 495 and volume expansion will connect the nano-gap, triggering the switch (FIG. 9). $Ag_2S$ is a semiconductor and also a good ionic conductor.

In operation, the sensors may be connected to low-power electronics. The electronics may have some on-board power. The power may be provided by a battery. Because of the very low power consumption of the sensor, the battery can last for a very long time (months, years, decades). Alternatively, the battery can be a rechargeable battery or the power can be supplied by a capacitor that are recharged through energy harvesting via photovoltaics, RF rectification, and the like. This can potentially lead to even longer lifetime.

Figure 10:
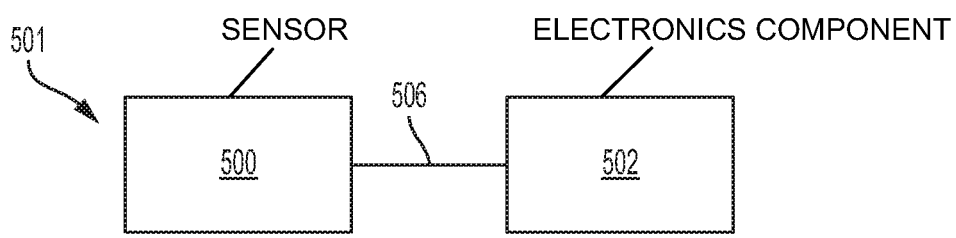
FIG. 10 illustrates a system for detecting a target gas in accordance with some embodiments of the present disclosure.

FIG. 10 illustrates a system 501 in accordance with some embodiments of the present disclosure. The system 501 includes a sensor 500 and an electronics component 502 in communication with the sensor. The sensor 500 is configured to generate a wake-up signal 506 to the electronics component 502. Until receiving the wake-up signal 506, the electronics component 502 may operate in a deep sleep mode to conserve energy. In some embodiments, the output of the sensor 500 is a voltage that is connected to a trigger input in the electronics component 502. In the sleep/standby mode, the system 501 may consume little or no power. The sensor 500 itself may use a little power as gas is accumulated, for example to provide charge to support redox reactions between the sensor and the gas.

The wake-up signal 506 can be triggered when the amount of accumulated target gas is sufficient for the electrical output signal (i.e., voltage) to pass a threshold that triggers the electronics component to wake up.

Figure 11:
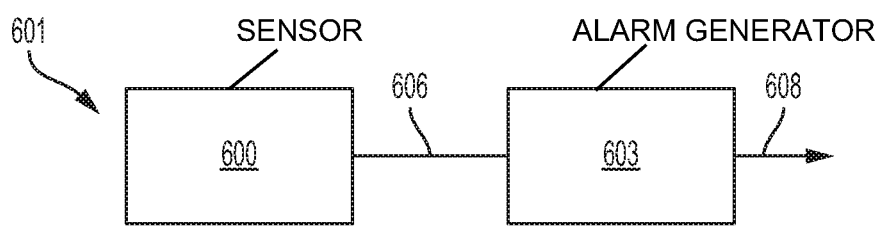
FIG. 11 illustrates a system for detecting a target gas in accordance with other embodiments of the present disclosure.

The electronics component may include an alarm generator. A non-limiting embodiment of a system 601 with an alarm generator 603 is depicted in FIG. 11. When the amount or concentration of target gas in the vicinity of the sensor 600 is sufficiently high, a wake-up signal 606 is generated which activates the alarm generator 603 from sleep/standby mode. The awakened alarm generator 603 generates an alarm signal 608.

The alarm signal 608 may be communicated on-site or off-site. The alarm signal 608 may be a wireless signal or be communicated by wire. In some embodiments, the alarm signal 608 is an audio or visual signal (e.g., a siren or flashing LED). In some embodiments, multiple alarm signals are generated. For example, an audio or visual signal may be generated to alert personnel on-site and a wireless signal may be generated to alert off-site personnel (e.g., at a central processing or command center). The transmission of the alarm signal(s) may or may not be low power. The alarm signal(s) may be transmitted directly or related via one or more intermediate nodes. The nodes individually or as a group may have wake-on features (e.g., wake-on radio frequency features) which allow the nodes to operate at extremely low power until receipt of the alarm signal. Upon receipt of the alarm signal, the nodes are awakened and retransmit the signal.

Figure 12:
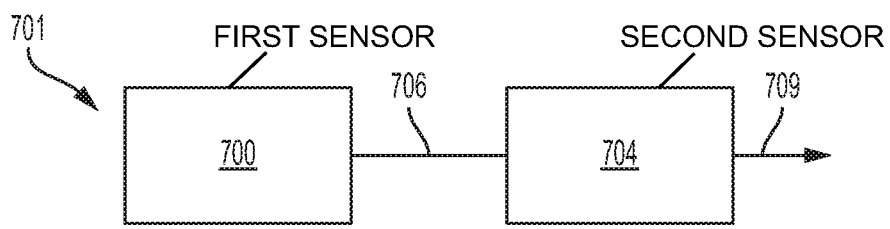
FIG. 12 illustrates a system for detecting a target gas in accordance with further embodiments of the present disclosure.

The electronics component may include a second sensor. A non-limiting embodiment of a system 701 with a second sensor 704 is depicted in FIG. 12. When the amount or concentration of target gas in the vicinity of the first sensor 700 is sufficiently high, a wake-up signal 706 is generated which activates the second sensor 704 from sleep/standby mode. The second sensor 704 may be a higher power-consuming and/or more sophisticated sensor. For example, the second sensor 704 may be more selective and/or more accurate. The second sensor 704 may be configured to ascertain whether the first sensor 700 was accurate in order to reduce/eliminate false positives. The second sensor 704 may alternatively or additionally be configured to determine the concentration of the target gas. The second sensor 704 may be used in combination with an alarm generator.

Figure 13:
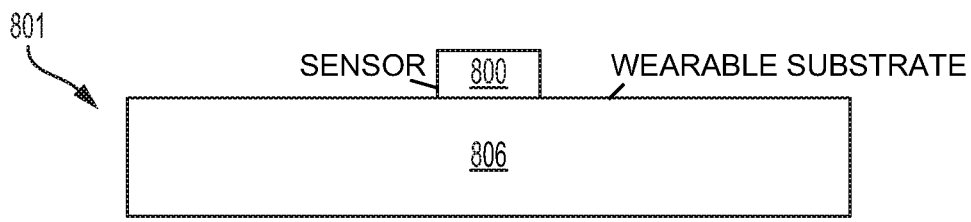
FIG. 13 illustrates a system for detecting a target gas in accordance with other embodiments of the present disclosure.

The target gas detection system may be wearable. FIG. 13 illustrates a non-limiting example of a wearable system 801. The system includes a wearable substrate 806 and a sensor 800 attached to the substrate 806. The substrate 806 may be any wearable article. Non-limiting examples include gloves, hats, helmets, socks, shoes, boots, pants, shorts, shirts, patches, and adhesive articles. In some embodiments, the substrate 806 is specially designed for to limit exposure to the target gas.

For example, the wearable substrate 806 may be or be applied to a hazardous materials suit or other protective garment designed to create a seal around a wearer. The sensor 800 may be located inside or outside the seal. In some embodiments, the system includes multiple sensors wherein at least one sensor is located outside the seal and at least one sensor is located inside the seal. In some embodiments, at least one sensor located outside the seal is configured to generate a wake-up signal to awaken at least one sensor located inside the seal. The at least one sensor located inside the seal may be a more sophisticated sensor than the at least one sensor located outside the seal or vice versa. In some embodiments, the sensor(s) external to the is/seal are configured to alert a wearer that he or she is entering an area where a target gas is present and the sensor(s) internal to the seal is/are configured to alert the wearer of a possible breach of the seal of the protective garment.

In some embodiments, multiple personnel (e.g., first responders, military, pipeline workers, gas company workers, etc.) will be at the site of a potential target gas emission (e.g., attack, leak, accident, etc.). A supervisor on-site or off-site (e.g., in a command center) may evaluate alarm signals and/or gas concentration data in conjunction with location data (e.g., GPS) from one or more of the personnel to identify a point source of the target gas emission and/or to narrow a search area.

In some embodiments, the systems of the present disclosure include multiple sensors for detecting and/or measuring the presence of multiple different gases. For example, the system may include at least one sensor for detecting a sulfide gas and at least one sensor for detecting hydrogen gas or a hydrocarbon gas (e.g., $CH_4$). Systems with sensors for detecting different gases may be useful for determining what type of event occurred (e.g., accident, leak, or attack). Such systems may also be useful for determining the best available treatment options for individuals or groups exposed to the gas(es).

Figure 14:
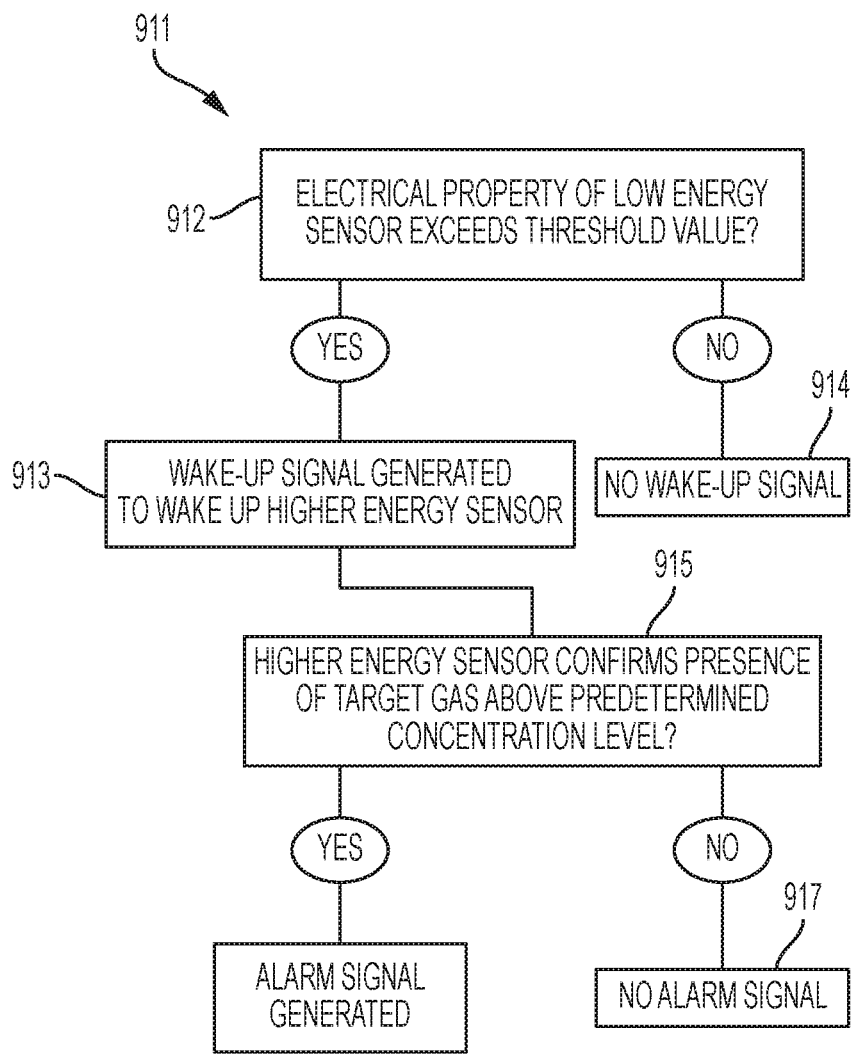
FIG. 14 is a flow chart illustrating a method for detecting a target gas in accordance with some embodiments of the present disclosure.

FIG. 14 is a flow chart for a non-limiting example of a method for detecting a target gas 911 in accordance with some embodiments of the present disclosure. The method 911 uses a system of the present disclosure. Initially, it is determined whether an electrical property from a low power sensor exceeds a predetermined threshold value 912. Exceeding the threshold value is indicative of the target gas being present at a concentration at or above a target gas limit. If the predetermined threshold value is not exceeded, then no wake-up signal is generated 914. In contrast, if the predetermined threshold value is exceeded, then a wake-up signal is generated 913. The wake-up signal is configured to activate an electronics component from stand-by mode. In the depicted embodiment, the electronics component includes a higher power, more sophisticated sensor. The second sensor verifies whether the first sensor was accurate or a false alarm 915. If the gas concentration level measured by the second sensor is indicative of a false alarm, then no alarm signal is generated 917. However, if the gas concentration level measured by the second sensor exceeds a predetermined level, then an alarm signal is generated 916. The predetermined gas concentration level for the second sensor may be set at the same level, a higher level, or a lower level in comparison to a concentration of target gas needed to trigger the first sensor. In addition to or as an alternative to triggering an alarm, the second sensor may continuously measure the target gas concentration level. Optionally, data concerning the target gas concentration level is transmitted off-site.

In some embodiments, the sensor is configured in a Wheatstone bridge configuration.

In some embodiments, the system is capable of being regenerated through a thermal, light, chemical, or electrochemical treatment.

It will be appreciated that variants of the above-disclosed and other features and functions, or alternatives thereof, may be combined into many other different systems or applications. Various presently unforeseen or unanticipated alternatives, modifications, variations or improvements therein may be subsequently made by those skilled in the art which are also intended to be encompassed by the following claims.

What is claimed is:

1. A system for detecting a target gas, the system comprising:
   a lower power-consuming sensor which exhibits an electrical property, wherein the electrical property changes in the presence of the target gas;
   a signal generator that generates a wake-up signal when a change in the electrical property passes a predetermined threshold value; and
   a higher power-consuming sensor configured to (A) operate in a sleep mode until the wake-up signal is received; and (B) continuously measure the presence of the target gas and communicate measurements off-site after the wake-up signal is received;
   wherein the lower power-consuming sensor comprises a capacitor comprising a dielectric material between a first capacitor electrode and a second capacitor electrode.

2. The system of claim 1, wherein the lower power-consuming sensor has a power consumption of 1 pW or less.

3. The system of claim 1, wherein the lower power-consuming sensor comprises a sensor material which chemically reacts with or expands in the presence of the target gas.

4. The system of claim 1, wherein the signal is a wireless signal, a wired signal, an audio signal, or a visual signal.

5. The system of claim 1, further comprising: an alarm generator for generating an alarm if the higher power-consuming sensor verifies the presence of the target gas.

6. The system of claim 1, further comprising: a wearable substrate, wherein the sensor is secured to the wearable substrate.

7. The system of claim 1, wherein the lower power-consuming sensor further comprises a fixed capacitor.

8. The system of claim 7, wherein at least one of the first electrode and the second electrode comprises palladium and wherein the target gas is hydrogen or methane.

9. The system of claim 1, wherein the dielectric material comprises a paste.

10. The system of claim 1, wherein the dielectric material comprises silver.

11. The system of claim 1, wherein the dielectric material comprises nanoparticles.

12. The system of claim 1, wherein the dielectric material comprises a paste containing silver.

13. The system of claim 1, wherein the dielectric material comprises silver nanoparticles.

14. The system of claim 1, wherein the dielectric material comprises a paste comprising silver nanoparticles.

15. The system of claim 1, further comprising: a wearable substrate.

16. The system of claim 15, wherein the wearable substrate is a hazardous materials suit.

17. The system of claim 15, wherein the wearable substrate is a protective garment designed to create a seal around a wearer.

18. The system of claim 17, wherein the lower power-consuming sensor is located external to the seal; and wherein the higher power-consuming sensor is located internal to the seal.

19. The system of claim 15, wherein the wearable substrate comprises an article selected from the group consisting of gloves, hats, helmets, socks, shoes, boots, pants, shorts, shirts, and patches.

20. A method for detecting a target gas, the method comprising: providing a system for detecting the target gas, the system comprising: a lower power-consuming sensor which exhibits an electrical property, wherein the electrical property changes in the presence of the target gas, wherein the lower power-consuming sensor is configured to generate a wake-up signal when the electrical property passes a predetermined threshold value; and a higher power-consuming sensor in communication with the lower power-consuming sensor and configured to (A) operate in a sleep mode until the wake-up signal is received; and (B) continuously measure the presence of the target gas and communicate measurements off-site after the wake-up signal is received.

* * * * *